US012453864B2

(12) United States Patent
Brown et al.

(10) Patent No.: US 12,453,864 B2
(45) Date of Patent: *Oct. 28, 2025

(54) EXTERNAL AUDITORY CANAL PHOTOBIOMODULATION DEVICE

(71) Applicant: Neuraxis, Inc., Versailles, IN (US)

(72) Inventors: Christopher R. Brown, Greensburg, IN (US); Mark T. Volz, Batesville, IN (US)

(73) Assignee: Neuraxis, Inc., Carmel, IN (US)

( * ) Notice: Subject to any disclaimer, the term of this patent is extended or adjusted under 35 U.S.C. 154(b) by 827 days.

This patent is subject to a terminal disclaimer.

(21) Appl. No.: 17/617,364

(22) PCT Filed: Jun. 23, 2020

(86) PCT No.: PCT/US2020/039040

§ 371 (c)(1),
(2) Date: Dec. 8, 2021

(87) PCT Pub. No.: WO2020/263767

PCT Pub. Date: Dec. 30, 2020

(65) Prior Publication Data

US 2022/0249860 A1 Aug. 11, 2022

Related U.S. Application Data

(60) Provisional application No. 62/866,763, filed on Jun. 26, 2019.

(51) Int. Cl.
*A61N 5/06* (2006.01)
*A61N 1/04* (2006.01)
*A61N 1/36* (2006.01)

(52) U.S. Cl.
CPC .... *A61N 5/0603* (2013.01); *A61N 2005/0605* (2013.01); *A61N 2005/0647* (2013.01);
(Continued)

(58) Field of Classification Search
CPC .... A61N 2005/0605; A61N 2005/0626; A61N 2005/0647; A61N 2005/0651;
(Continued)

(56) References Cited

U.S. PATENT DOCUMENTS 5,084,007 A 1/1992 Malin et al.
8,308,784 B2 11/2012 Streeter et al.
(Continued)

FOREIGN PATENT DOCUMENTS

JP 2014505509 A 3/2014
KR 20140006236 A * 1/2014 ............. A61N 5/067
(Continued)

OTHER PUBLICATIONS

Chandran V. Seshagiri et al; Response Properties of Neighboring Neurons in the Auditory Midbrain for Pure-Tone Stimulation: A Tetrode Study; J Neurophysiol 98: 2058-2073, 2007.
(Continued)

*Primary Examiner* — Shirley X Jian
*Assistant Examiner* — Vynn V Huh
(74) *Attorney, Agent, or Firm* — Barnes & Thornburg LLP

(57) ABSTRACT

A photobiomodulation device may include a housing configured to be inserted into an external auditory meatus of a human ear, at least a one irradiation source coupled to the housing such that at least a portion of a radiation emitting surface thereof faces at least a portion of dermis of the external auditory meatus of the ear beneath which at least one of an arterial branch and a peripheral nerve branch of at least one cranial nerve is located, and an electrical circuit carried by the housing and configured to control the at least one radiation source to irradiate the at least one of the arterial branch and the peripheral nerve branch of the at least
(Continued)

one cranial nerve through the at least a portion of dermis of the external auditory meatus of the ear.

20 Claims, 6 Drawing Sheets

(52) U.S. Cl.
CPC ................. *A61N 2005/0651* (2013.01); *A61N 2005/0663* (2013.01); *A61N 2005/0664* (2013.01)

(58) Field of Classification Search
CPC .... A61N 2005/0662; A61N 2005/0663; A61N 5/0603; A61N 5/0622; H04R 1/02; H04R 1/028; H04R 1/1016; H04R 1/1041
USPC .......... 607/1–95, 115–156, 88–94; 606/2–19
See application file for complete search history.

(56) References Cited

U.S. PATENT DOCUMENTS

| | | | |
|---|---|---|---|
| 8,535,361 | B2 | 9/2013 | Lim et al. |
| 9,258,642 | B2 | 2/2016 | Nissila et al. |
| 2008/0146549 | A1 | 6/2008 | Coleman |
| 2012/0253427 | A1 | 10/2012 | Aunio et al. |
| 2013/0301851 | A1* | 11/2013 | Nissila ................. A61N 5/0618 381/74 |
| 2015/0112405 | A1 | 4/2015 | Brown et al. |
| 2015/0112411 | A1 | 4/2015 | Beckman |
| 2018/0200522 | A1 | 7/2018 | Taca, Jr. |
| 2018/0256917 | A9 | 9/2018 | Lim |
| 2018/0280721 | A1 | 10/2018 | Beckner et al. |
| 2022/0072311 | A1 | 3/2022 | Taca, Jr. |

FOREIGN PATENT DOCUMENTS

| | | | |
|---|---|---|---|
| WO | 2015/008154 | A2 | 1/2015 |
| WO | 2016/151377 | A1 | 9/2016 |
| WO | 2017/044967 | A1 | 3/2017 |
| WO | 2019/053625 | A1 | 3/2019 |

OTHER PUBLICATIONS

Hector D. Orozco Perez, et al; Binaural Beats through the Auditory Pathway: From Brainstem to Connectivity Patterns; National Center for Biotechnology Information eNeuro; Mar. 11, 2020.
John H. Grose, et al; Binaural beat salience; National Center for Biotechnology Information; Feb. 6, 2012.
Kim Byung-Hyun, et al; The Effect of White Noise and Pink Noise on the Brain Activity; The Journal of the Korea Contents Association; 2017 (English Google Machine Translation Appended).
Leila Chaieb, et al; Auditory beat stimulation and its effects on cognition and mood states; Frontiers in Psychiatry; May 12, 2015.
Michelle T. Graham, et al; Simulations and human cadaver head studies to identify optimal acousiitic receiver locations for minimally invasive photoacoustic-guided neurosurgery; Photoacoustics; May 16, 2020.
Miguel Garcia-Argibay, et al; Efficacy of binaural auditory beats in cognition, anxiety, and pain perception: a meta-analysis; Psychological Research; Aug. 2, 2018.
Patrick A. Mcconnell, et al; Auditory driving of the autonomic nervous system: Listening to theta-frequency binaural beats post-exercise increases parasympathetic activation and sympathetic withdrawal; Frontiers in Psychology; Nov. 14, 2014.
Qun Wei et al; Novel design of smart sleep-lighting system for improving the sleep environment of children; Technology and Health Care; Jun. 18, 2019; 27(suppl 1); 3-13.
R. Padmanabhan, et al; A prospective, randomised, controlled study examining binaural beat audio and pre-operative anxiety in patients undergoing general anaesthesia for day case surgery; Anaesthesia; Jul. 7, 2005; vol. 60, Issue 9; p. 874-877.
Ramaswamy Palaniappan, et al; On the binaural brain entrainment indicating lower heart rate variability; International Journal of Cardiology; Apr. 22, 2015; vol. 190, pp. 262-263.
Vasileios Gkolias, et al; Reduced pain and analgesic use after acoustic binaural beats therapy in chronic pain—A double-blind randomized control cross-over trial; European Pain Federation; Jul. 27, 2020.
Vera Abeln, et al; Brainwave entrainment for better sleep and post-sleep state of young elite soccer players—A pilot study; European Journal of Sport Science, 2014; vol. 14, No. 5, 393-402.
Vernon Furtado Da Silva, et al.; Stimulation by Light and Sound: Therapeutics Effects in Humans. Systematic Review; Clinical Practice and Epidemiology in Mental Health; Jun. 25, 2015.
Miranda, Adrian, and Arturo Taca. "Neuromodulation with percutaneous electrical nerve field stimulation is associated with reduction in signs and symptoms of opioid withdrawal: a multisite, retrospective assessment." The American journal of drug and alcohol abuse vol. 44,1 (2018): 56-63. doi:10.1080/00952990.2017.1295459.
Roberts, Arthur and Christopher R. Brown. "Percutaneous Peri-Auricular Peripheral Nerve Field Stimulation: A Novel, Non-Opioid Therapy for Diabetic Neuropathy." The Pain Practitioner, vol. 25, 3 (2015): 41-47.
PCT International Search Report and Written Opinion completed by the ISA/US on Aug. 26, 2020 and issued in connection with PCT/US2020/039040.
Non-Final Office Action issued by the USPTO on Sep. 11, 2024, for U.S. Appl. No. 17/589,082 (33 pages).
Response to Non-Final Office Action filed with the USPTO on Dec. 2, 2024, for U.S. Appl. No. 17/589,082 (14 pages).
Final Office Action issued by the USPTO on Mar. 25, 2025, for U.S. Appl. No. 17/589,082 (21 pages).
Response to Final Office Action and Request for Continued Examination filed with the USPTO on Jun. 25, 2025, for U.S. Appl. No. 17/589,082 (14 pages).
Non-Final Office Action issued by the USPTO on Sep. 27, 2024, for U.S. Appl. No. 17/861,646 (62 pages).
Response to Non-Final Office Action filed with the USPTO on Dec. 12, 2024, for U.S. Appl. No. 17/861,646 (19 pages).
Final Office Action issued by the USPTO on Apr. 3, 2025, for U.S. Appl. No. 17/861,646 (54 pages).
Response to Final Office Action and Request for Continued Examination filed with the USPTO on Jun. 25, 2025, for U.S. Appl. No. 17/861,646 (17 pages).

* cited by examiner

EXTERNAL AUDITORY CANAL PHOTOBIOMODULATION DEVICE

CROSS-REFERENCE TO RELATED APPLICATION

This application is a U.S. national stage entry of International Application Serial No. PCT/US2020/039040, filed Jun. 23, 2020, which claims the benefit of, and priority to, U.S. Provisional Patent Application Ser. No. 62/866,763, filed Jun. 26, 2019, the disclosures of which are expressly incorporated herein by reference in their entireties.

TECHNICAL FIELD

The present disclosure relates generally to photobiomodulation devices, and more specifically to such devices configured to be inserted into the external auditory canal (also known as the external auditory meatus) of at least one ear of a human or animal.

BACKGROUND

Pulsed Near-Infrared Photobiomodulation (PNIP) is a technique which uses radiant light energy to modify biological systems with a resulting therapeutic effect. PNIP is known to affect the cranial arteries, nerves, cranial perfusion pressure, and modulate neural oscillations when delivered both transcranially and intra-nasally. Pulsed, rather than steady or static radiation, is believed to reduce the potential over-heating of the adjacent tissues.

Chromophores contain both heme and copper centers which absorb light in the infra-red and near infra-red regions. It is hypothesized that photons disassociate inhibitory nitric oxide leading to an increase in electron transport, mitochondrial membrane potential, ATP production and concurrently activate light-sensitive ion channels allowing calcium to enter the cell after initial photon absorption activates signaling pathways. This acts as a vasodilator and increases lymphatic flow. As a result, the above-noted initial beneficial therapeutic effects of PNIP may be a result of increases in cerebral blood flow (CBF), oxygen consumption, oxygen availability, and increased ATP activity in the mitochondria. While vasodilation reverses shortly after the light stimulation is removed, the changes following exposure to light are known to last for days, weeks, or even months. The long-lasting effects cannot be explained simply by the activation of the mitochondria or stimulation of blood flow alone and is postulated to be as a result of activation of signaling pathways and transcription factors that change protein expression.

SUMMARY

The present disclosure may comprise one or more of the features recited in the attached claims, and/or one or more of the following features and combinations thereof. In one aspect, a photobiomodulation device may comprise a housing having a first portion configured to be inserted into an external auditory meatus of a human ear and a second portion, at least one irradiation source coupled to the first portion of the housing such that at least a portion of a radiation emitting surface thereof faces at least a portion of dermis of the external auditory meatus beneath which at least one of an arterial branch and a peripheral nerve branch of at least one cranial nerve is located, and an electrical circuit carried by the second portion of the housing and electrically connected to the at least one irradiation source, the electrical circuit including at least one circuit component for controlling the at least one irradiation source to irradiate the at least one of the arterial branch and the peripheral nerve branch of the at least one cranial nerve through the at least a portion of dermis of the external auditory meatus.

In another aspect, a photobiomodulation system may comprise the photobiomodulation device described herein, wherein the at least one circuit component includes wireless communication circuitry, and a mobile communication device including wireless communication circuitry configured to communicate wirelessly with the wireless communication circuitry of the photobiomodulation device, the mobile communication device further comprising a processor programmed to control operation of the photobiomodulation device by wirelessly communicating operating instructions thereto.

In yet another aspect, a photobiomodulation system may comprise the photobiomodulation device described herein, and a mobile communication device hard-wire connectable to the photobiomodulation device and including a processor programmed to control operation of the photobiomodulation device by communicating operating instructions to the at least one circuit of the photobiomodulation device with the mobile communication device hard-wire connected to the photobiomodulation device.

In a further aspect, a photobiomodulation apparatus may comprise a first photobiomodulation device having a first housing configured to be inserted into an external auditory meatus of one ear of a human, at least a first irradiation source coupled to the first housing such that at least a portion of a radiation emitting surface thereof faces at least a portion of dermis of the external auditory meatus of the one ear beneath which at least one of an arterial branch and a peripheral nerve branch of at least one cranial nerve is located, and a first electrical circuit carried by the first housing and configured to control the at least a first radiation source to irradiate the at least one of the arterial branch and the peripheral nerve branch of the at least one cranial nerve through the at least a portion of dermis of the external auditory meatus of the one ear.

DESCRIPTION OF THE ILLUSTRATIVE EMBODIMENTS

For the purposes of promoting an understanding of the principles of this disclosure, reference will now be made to a number of illustrative embodiments shown in the attached drawings and specific language will be used to describe the same.

Figure 1A:
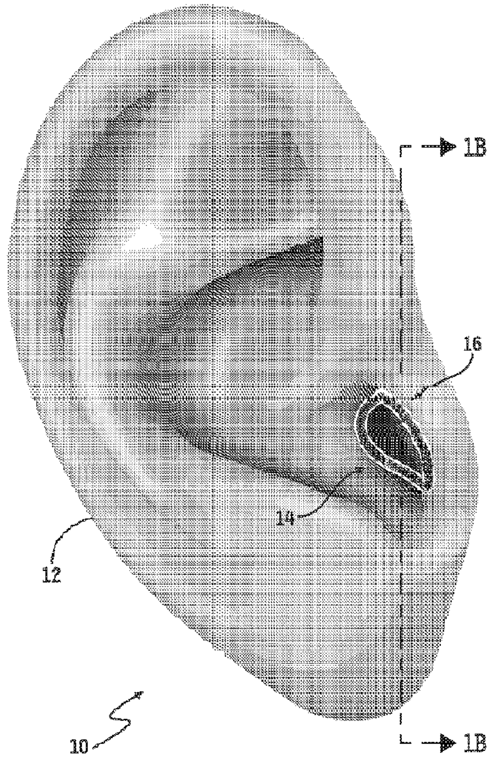
FIG. 1A is a perspective view of a human ear illustrating auricular innervation in and about an external entrance of the external auditory meatus.
Figure 1B:
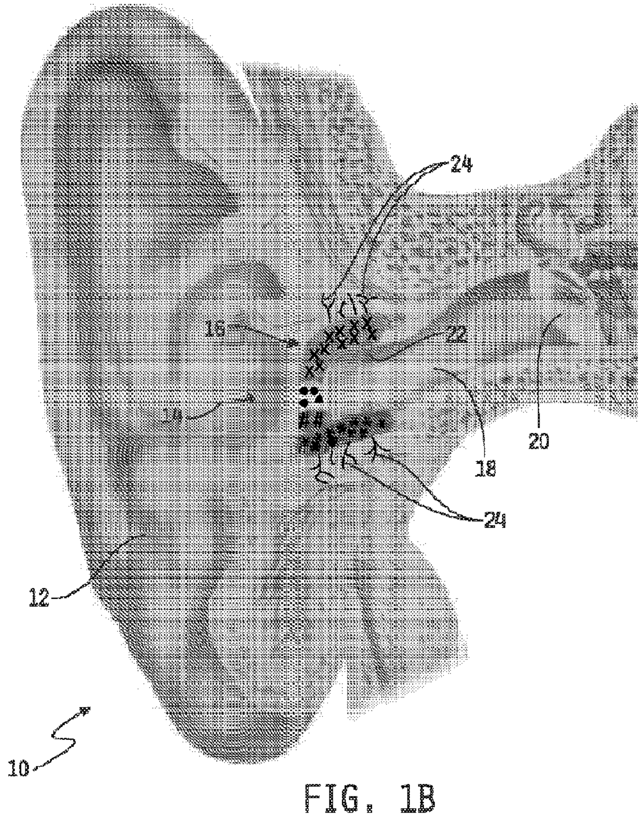
FIG. 1B is a partial cross-sectional view of the human ear of FIG. 1A as viewed along section lines 1B-1B thereof, illustrating distribution of cranial nerves V (*), VII (#), IX (●) and X (X) and arterial branches about the external entrance of the external auditory meatus and extending at least partially into the external auditory meatus.

This disclosure relates to devices and techniques for irradiating at least a portion of the external auditory meatus of a human or animal ear for the purpose of stimulating a peripheral branch of at least one cranial nerve and/or stimulating at least one arterial branch anatomically located beneath the dermis in the external auditory meatus. Referring to FIGS. 1A and 1B, for example, a human ear 10 is shown depicting the auricle 12 and an entrance opening 14 to the external auditory meatus 18 defined and extending between the entrance opening 14 and the tympanic membrane 20. As illustrated by example in FIGS. 1A and 1B, peripheral branches of a number of cranial nerves 16 extend about the periphery of the entrance opening 14 and at least partially into the external auditory meatus 18 beneath the dermis 22. In particular, a peripheral branch of the trigeminal nerve (sometimes referred to as "V"), depicted in FIGS. 1A and 1B as "*," extends along an arcuate anterior portion of the entrance opening 14 and at least partially into the external auditory meatus 18. Likewise, a peripheral branch of the vagus nerve (sometimes referred to as "X"), depicted in FIGS. 1A and 1B as "X," extends along an arcuate posterior portion of the entrance opening 14 and at least partially into the external auditory meatus 18. Top and bottom peripheral branches of the facial nerve (sometimes referred to as "VII"), depicted in FIGS. 1A and 1B as "#," extend along top and bottom portions of the entrance opening 14 next to opposite arcuate ends of the trigeminal nerve V (*), and top and bottom peripheral branches of the glossopharangeal nerve (sometimes referred to as "IX"), depicted in FIGS. 1A and 1B as "●," extend along top and bottom portions of the entrance opening 14 next to opposite arcuate ends of the vagus nerve X (X) and next to respective top and bottom peripheral branches of the facial nerve VII (#). As illustrated by example in FIG. 1B, the facial nerve branches VII (#) and the glossopharangeal nerve branches IX (●) both extend at least partially into the external auditory meatus 18 from the entrance opening 14, although the trigeminal nerve branch V (*) and the vagus nerve branch X (X) each extend substantially further into the external auditory meatus 18 by comparison. Arterial branches 24 are also illustrated in FIG. 1B extending at least partially about the external auditory meatus 18 in and/or adjacent to the region containing the cranial nerves 16.

Figure 2A:
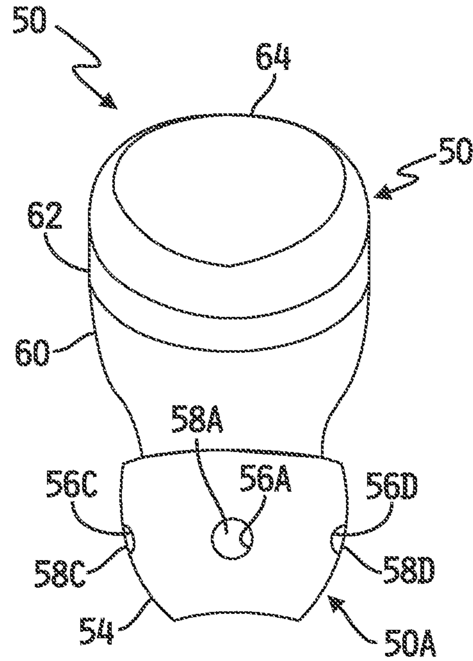
FIG. 2 includes FIGS. 2A-2D which illustrate various views of an embodiment of an external auditory canal photobiomodulation device.
Figure 2B:
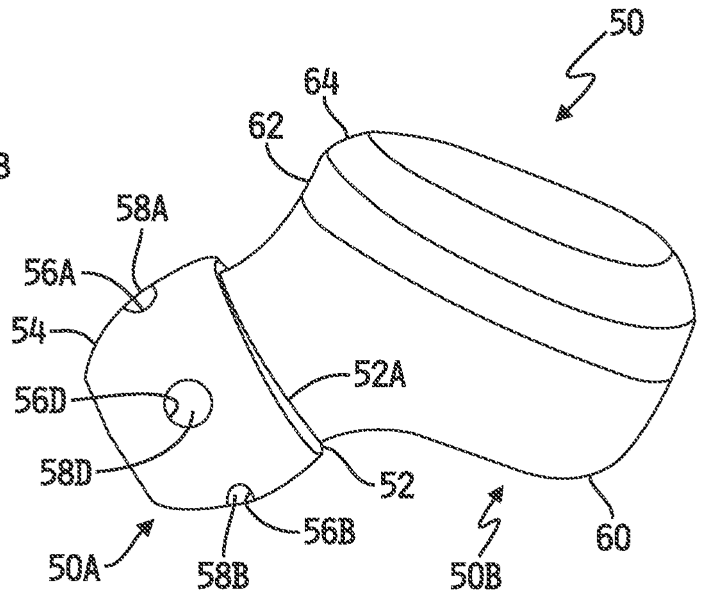
Figure 2C:
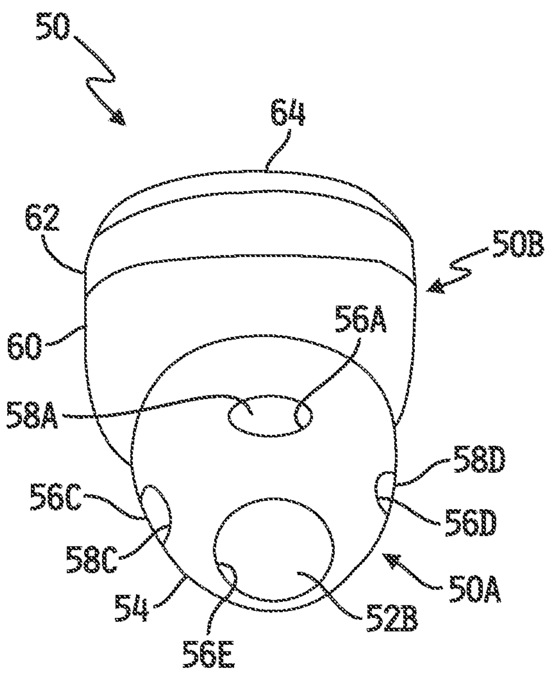
Figure 2D:
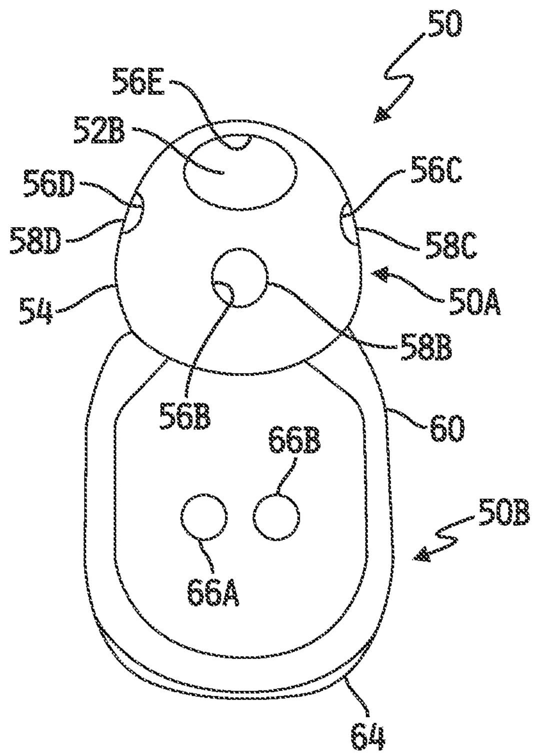
Figure 3:
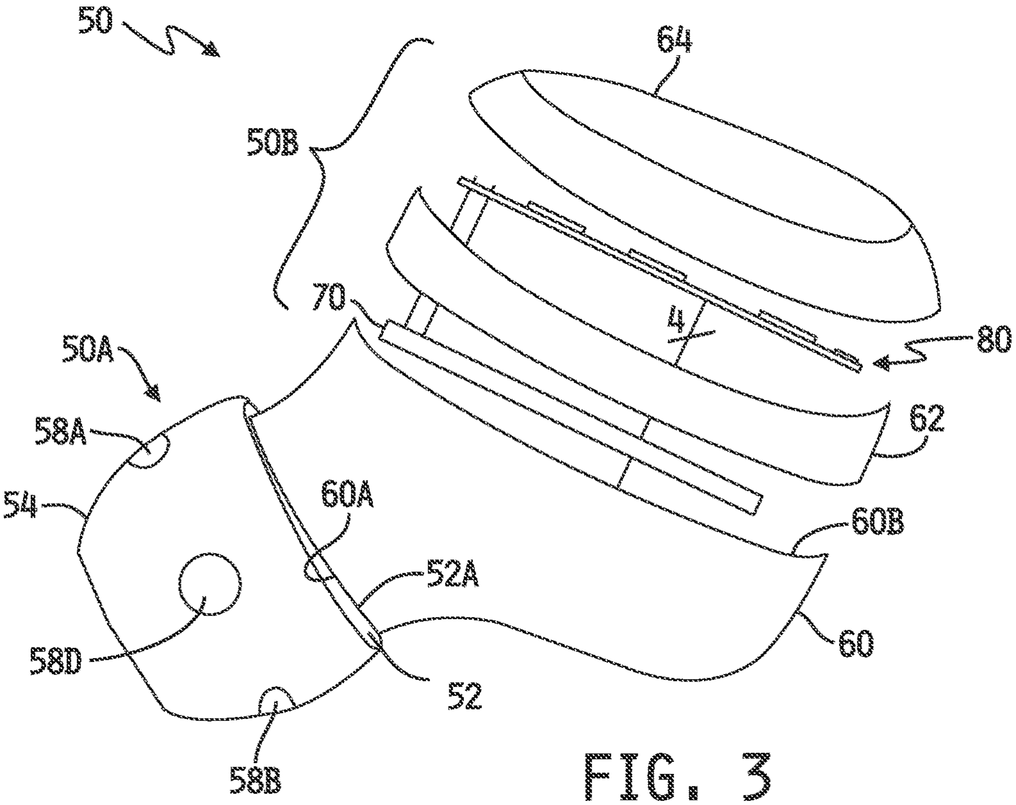
FIG. 3 is a partial assembly view of the external auditory canal photobiomodulation device of FIGS. 2A-2D showing placement of a power source and control circuitry within a housing of the device.
Figure 4:
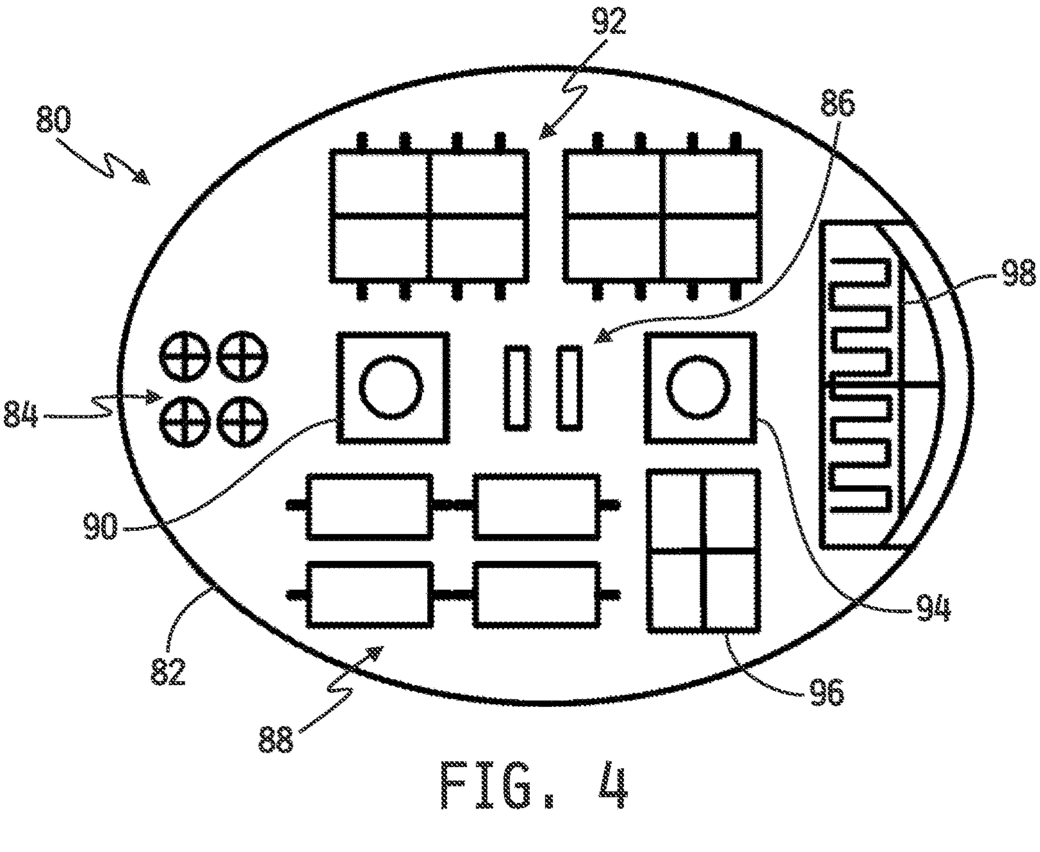
FIG. 4 is a top plan view of an embodiment of the control circuitry of the external auditory canal photobiomodulation device illustrated in FIG. 3.

Referring now to FIGS. 2A-2D an embodiment is shown of a photobiomodulation device 50 configured to be placed in transdermal contact with the external auditory meatus 18 of a human ear 10 at the external opening 14 thereto, and to be controlled to irradiate at least one of the peripheral branches of one or more of the cranial nerves 16 and/or of one or more arterial branches 24 extending about the periphery of the entrance opening 14 and at least partially into the external auditory meatus 18 beneath the dermis 22. In some embodiments, only a single such device 50 is implemented, although in other embodiments two such devices 50 are implemented; one inserted into each ear of the user. In the illustrated embodiment, the device 50 includes an external auditory meatus insertion portion 50A implemented in a form similar to a conventional "earbud," and a control portion 50B including a source of electrical power as well as control and wireless communication electronics. Examples of the latter are illustrated in FIGS. 3 and 4 which will be described in detail below.

The external auditory meatus insertion portion 50A illustratively includes a generally curved, e.g., dome-shaped, housing 52 having an open end 52A and a curved outer surface which illustratively tapers downwardly in cross-section toward an opposite end 52B thereof, wherein the housing 52 is generally sized and configured to be received, leading with the end 52B, through the entrance opening 14 and at least partially into the external auditory meatus 18 of a human ear 10. In some embodiments, a flexible ear tip or ear cap 54 is provided, which is generally shaped similarly to the housing 52 and within which the housing 52 is received. In such embodiments, the ear tip or cap 54 may illustratively be formed of silicone or other material(s) configured facilitate frictional transdermal engagement of the ear tip or cap 54 with the tissue lining extending circumferentially about the entrance opening 14 and along the external auditory meatus 18 adjacent thereto. In some alternate embodiments in which other conventional structure(s) is/are provided for releasably attaching or affixing the device 50 to the ear 10, the ear tip or cap 54 may be omitted. In any case, the external auditory meatus insertion portion 50A in such embodiments may be sized to be received into, but not necessarily engage, the entrance opening 14 and at least a portion of the external auditory meatus 18 adjacent thereto. In some such embodiments, the external auditory meatus insertion portion 50A may contact but not frictionally engage the entrance opening 14 and/or at least a portion of the external auditory meatus 18 adjacent thereto, and in other such embodiments the device 50 may be designed such that the external auditory meatus insertion portion 50A is insertable through the opening 14 and at least partially into the external auditory meatus 18 but does not contact the entrance opening 14 and/or the external auditory meatus 18 adjacent thereto.

The housing 52 and ear tip or cap 54 (in embodiments which include the ear tip or cap 54) define a number of openings therethrough each sized to receive therein one of a corresponding number of irradiation sources, such that a radiation emitting surface of each of the number of irradiation sources faces a respective portion of the entrance opening 14 and/or at least a portion of the external auditory meatus 18 adjacent thereto. In alternate embodiments, the housing 52 and ear tip or cap 54 (in embodiments which include the ear tip or cap 54) may not define openings per se in which a respective irradiation source is received, but may instead define locations at or in which a respective irradiation source is mounted. In such embodiments, the housing 52 and/or ear tip or cap 54 may define one or more light transmissive portions or windows through which radiation produced by respective ones of the irradiation source may be focused or otherwise transmitted to the peripheral branches of one or more of the cranial nerves 16 and/or toward one or more of the arterial branches 24. In any case, each of the number of irradiation sources illustratively directs radiation produced thereby toward a respective one or more of the peripheral branches of one or more of the cranial nerves 16 and/or toward a respective one or more arterial branches 24 extending about the periphery of the entrance opening 14 and at least partially into the external auditory meatus 18 beneath the dermis 22.

In the illustrated embodiment, four such openings 56A-56D are spaced, e.g., equidistant from one another, radially about the housing 52 and ear tip or cap 54, and four corresponding irradiation sources 58A-58D, e.g., each in the form of a light emitting diode (LED), are provide with each inserted into a respective one of the openings 56A-56D. In this embodiment, the device 50 is illustratively orientable to position each of the irradiation sources 58A-58D opposite to, and facing, the peripheral branches of a respective at least one of the cranial nerves 16 and/or of a respective at least one of the arterial branches in or adjacent to the region containing the cranial nerves 16. For example, the device 50 is illustratively positionable relative to the external auditory meatus 18 such that the irradiation source 58A is opposite the peripheral branches of the cranial nerves VII (#) and IX (●) at the top of the external auditory meatus 18, the irradiation source 58B is opposite the peripheral branches of the cranial nerves VII (#) and IX (●) at the bottom of the external auditory meatus 18, the irradiation source 58C is opposite the peripheral branches of the cranial nerve V (*) at the anterior portion of the external auditory meatus 18 and the irradiation source 58D is opposite the peripheral branches of the cranial nerve X (X) at the posterior portion of the external auditory meatus 18 (e.g., see FIG. 5). One or more of the irradiation sources 58A-58D so positioned may additionally irradiate one or more arterial branches 24 in or adjacent to the various regions of the external auditory meatus 18 containing the respective cranial nerves 16.

It will be understood that above-described positioning of the device 50 is provided only as an illustrative example, and other positions or orientations of the device 50 relative to the external opening 14 and/or to at least a portion of the external auditory meatus 18 adjacent thereto are intended to fall within the scope of this disclosure. It will also be understood that whereas the embodiment illustrated in FIGS. 2A-2D includes four irradiation sources 58A-58D equally-spaced apart radially about the housing 52, alternate embodiments may include more or fewer such irradiation sources equally or non-equally spaced apart radially or otherwise positioned about the housing 52.

It is believed that auricular arterial branches and nerve bundles absorb radiation in the frequency range of red visible light, and reflect radiation in the blue and green frequency ranges. In one example embodiment, the irradiation sources 58A-58D are thus each configured to produce radiation at a frequency, or in the frequency range, of red visible light. In one particular embodiment, the irradiation sources 58A-58D are each illustratively configured to produce radiation at 630 nm. It will be understood, however, that one or more of the irradiation sources 58A-58D may alternatively be configured to produce radiation at any frequency in the frequency range of red visible light, or alternatively still be configured to produce radiation at any frequency in any range of frequencies visible or otherwise. It will be further understood that while the irradiation sources 58A-58D have been described in one embodiment as being implemented in the form of LEDs, one or more of the irradiation sources 58A-58D may alternatively be provided in the form of one or any combination of other conventional irradiation sources configured to produce radiation at any single frequency or in any range of frequencies.

In the illustrated embodiment, the ear tip or cap 54 illustratively includes an axial opening 56E therethrough, e.g., to promote flexibility of the ear tip or cap 54 and/or facilitate frictional fitting of the external auditory meatus insertion portion 50A to the entrance opening 14 and/or at least an adjacent portion of the external auditory meatus 18 of the ear 10. In some embodiments, as illustrated by example in FIGS. 2C and 2D, the opening 56E exposes the domed end 52B of the housing 52. In alternate embodiments, the housing 52 may include a speaker, e.g., a voice coil, magnet and acoustic chamber or other conventional speaker and/or one or more other acoustic devices, and the opening 56E may expose such a speaker to the external auditory meatus 18. In such embodiments, the device 50 may include suitable electronics configured to reproduce sound via the speaker and/or one or more other acoustic devices, e.g., music, speech and/or other audio content. It will be understood that, in some such embodiments in which the housing 52 includes one or more acoustic devices, any such one or more acoustic devices may be or include any device for amplifying and/or transmitting electromagnetic radiation at any frequency or range of frequencies which can be heard, felt and/or otherwise perceived, consciously and/or unconsciously, by a human or other animal. One non-limiting example of such a frequency range may be 20 Hz-20 kHz, although other non-limiting examples may include one or more frequencies below 20 Hz and/or one or more frequencies above 20 kHz, and may generally include one or more frequencies of vibration, sound, ultrasound and/or infrasound.

The control portion 50B of the device 50 illustratively includes a housing 60 having an open end 60A coupled to the open end 52A of the housing 52 of the external auditory meatus insertion portion 50A, and another open end 60B spaced apart from the end 60A. The housing 60 illustratively includes a circuit board carrier sleeve 62 removably coupled to the open end 60B thereof, and a cover 64 removably coupled to the carrier sleeve 62. The housing 60 defines a cavity therein that is illustratively sized to receive, via the open end 60B, a source 70 of electrical power, as illustrated by example in FIG. 3.

In one embodiment, the source 70 of electrical power is implemented in the form of a conventional battery. In some such embodiments, the battery 70 may be rechargeable, and in such embodiments the housing 60 may define openings on the underside thereof via which battery recharging terminals 66A, 66B may be accessed for charging the battery 70, as illustrated by example in FIG. 2D. In alternate embodiments, the battery 70 may be non-rechargeable. In still other embodiments, the source 70 of electrical power may be implemented in the form of one or more other conventional sources of electrical power 70 other than, or in addition to, a battery. In one specific embodiment in which the source 70 of electrical power is provide in the form of a conventional, rechargeable battery, such a battery 70 may be provided in the form of a 3.7 volt, flat pack, 50 mah (milliampere-hours) Lithium battery, although it will be understood that such a specific implementation is described only by way of example, and that the battery 70 may be configured to produce greater or lesser voltage, greater or lesser energy capacity and/or be formed of other active elements and/or compounds. In some alternate embodiments in which the device 50 is hard-wire connected to an electronic control device, e.g., as illustrated by example in FIG. 7 and as described below, electrical power may be supplied by the electronic control device to the device 50. In some such embodiments, the source 70 of electrical power may be omitted.

Referring again to FIG. 3, an electrical circuit 80 is illustratively mounted to and within the circuit board carrier sleeve 62, and the cover 64 is then mounted to the sleeve 62 such that the housing 60 carries the source 70 of electrical power and the electrical circuit 80. In some embodiments, the housing 52 and the housing 60 are separate components attached, connected or otherwise coupled together as described above. In alternative embodiments, the housings 52, 60 may be merged together into a single, unitary housing. In either case, the housing 52 illustratively represents one housing portion configured to be inserted into the external auditory meatus 18 of the ear 10, and the housing 60 represents another housing portion configured to carry the source 70 of electrical power and the electrical circuitry 80.

Referring now to FIG. 4, an embodiment of the electrical circuit 80 is shown. In the illustrated embodiment, the electrical circuit 80 includes a circuit board 82 having a number of different circuit components mounted thereto. The circuit board 82 may illustratively be a conventional rigid, semi-flexible or flexible circuit board configured for surface-mounting and/or through-hole mounting of circuit components thereto. For example, the circuit board 82 illustratively includes electrical terminals or pads 84 configured for connection of electrical power leads or wires thereto. In the embodiment illustrated in FIG. 3, for example, positive (+) and negative (or ground) (−) terminals of the source 70 of electrical power are connected to suitable wires which extend through the circuit board carrier sleeve 62 and into electrical connection with the terminals or pads 84. The circuit board 86 further includes irradiation source terminals 86 or pads configured for connection of irradiation source leads or wires thereto. In the embodiment illustrated in FIG. 3, for example, each of four wires connected to a different respective one of the irradiation sources 58A-58D extends through the open end 52A of the housing 52 of the external auditory meatus insertion portion 50A and into the open end 60A of the housing 60, and then through the circuit board carrier sleeve 62 and into electrical connection with the terminals or pads 86.

Four resistors 88 are mounted to the circuit board 82, and each is electrically coupled at one end through a normally-off switch 90 to the electrical power terminals 84, and each is electrically connected at an opposite end through the terminals or pads 86 to a different respective one of the four irradiation sources 58A-58B. The switch 90 is controllable to an on position, as will be described below, to electrically connect the source 70 of electrical power through the resistors 88 to the irradiation sources 58A-58D to cause the irradiation sources 58A-58D to emit radiation. In one example embodiment in which the source 70 of electrical power is the 3.7 volt battery described above, the irradiation sources 58A-58D are each implemented in the form of a 630 nm, 2 volt, 20 mA, 0.06 Watt LED having a luminance intensity of 240 mcd (milli-candela) and a 120 degree viewing angle, and in this embodiment each of the resistors 88 is implemented in the form of a 60 ohm, 0.25 Watt, +/−1% tolerance, metal film resistor. It will be understood, however, that such an implementation of the irradiation sources 58A-58D and of the resistors 88 is provided only by way of example, and that other irradiation sources 58A-58D and/or other values and/or other specifications of the irradiation sources 58A-58D and/or of the resistors 88 may alternatively be used.

The electrical circuit 80 further illustratively includes a number of integrated circuits 92 mounted to the circuit board 82. In some embodiments, at least one of the integrated circuits 92 is electrically connected to the switch 90 and is configured to control the switch 90 between on and off states at a predefined or programmable switching rate. In one example embodiment, which should not be considered to be limiting in any way, the switching rate is approximately 40 Hz, although other switching rates, or varying switching rates, may alternatively be used. In some such embodiments, the duty cycle of the switching rate is approximately 50%, although in other embodiments the duty cycle may be greater or less than 50%. In some embodiments, one or more of the integrated circuits 92 may control the duty cycle, and in some such embodiments the duty cycle may be programmable or variable. In some embodiments, at least one of the integrated circuits 92 is a conventional driver circuit operatively coupled to the source 70 of electrical power, the switch 90 and/or the resistors 88, and is operable to supply electrical power, and in some embodiments regulate voltage and/or current, from the source 70 of electrical power to the irradiation sources 58A-58D.

The electrical circuit 80 further illustratively includes an on/off switch 94 mounted to the circuit board 82. In some embodiments in which the device 50 is self-controlled, a manually-selectable actuator accessible externally to the housing 60 may be operatively coupled to the switch 94, and the device 50 may be powered on and off via manual actuation of such an actuator. In other embodiments, the device 50 may be hard-wire connected to a remotely located control device, e.g., a mobile or stationary electronic control device, e.g., as illustrated by example in FIG. 7, and in such embodiments the switch 94, and in some cases one or more of the integrated circuits 92, may be electrically connected to the control device, such that the control device hard-wire connected to the device 50 controls operation of the device 50. As described above, in some such embodiments, electrical power may be supplied by the control device to the device 50 through the hard-wire connection, and in such embodiments the power source 70 may (or may not) be omitted from the device 50. Examples of the remotely located control device may include, but are not limited to, a laptop, tablet or personal computer, a mobile communication device such as a mobile phone, smart watch or the like, or other mobile or stationary electronic control device or system.

In still other embodiments, the device 50 is configured to be wirelessly controlled by a wirelessly-connected control device, and in such embodiments wireless communication circuitry may be mounted to the circuit board 82 and electrically connected to at least the switch 94. Such an embodiment is illustrated by example in FIG. 4, in which a wireless communication control circuit 96 is mounted to the circuit board 82 and electrically connected to the switch 94 (either directly or via one or more of the integrated circuits 92), and a wireless communication antenna 98 is also mounted to the circuit board 82 and electrically connected to the wireless communication circuit 96. In one such embodiment, the wireless communication circuit 96 is illustratively implemented in the form of a conventional Bluetooth® controller, and the antenna 98 is a conventional Bluetooth® antenna array, and the Bluetooth® controller 96 is operable in a conventional manner to receive and, in some embodiments, to transmit information in accordance with a conventional Bluetooth® communication protocol. It will be understood, however, that Bluetooth® represents only one example wireless communication protocol that may be implemented in the device 50, and that in alternate embodiments the wireless communication control circuit 96 and antenna 98 may be configured for wireless communication in accordance with one or more other conventional wireless communication protocols.

In embodiments in which the electrical circuit 80 includes wireless communication circuitry as illustrated by example in FIG. 4 and described above, a mobile communication device (MCD) is illustratively provided and programmed to control operation of the photobiomodulation device 50 via instructions communicated wirelessly thereto. Such a programmed MCD may also be used to control operation of the photobiomodulation device 50 in embodiments in which the device 50 is hard-wire connected to the MCD.

Figure 5:
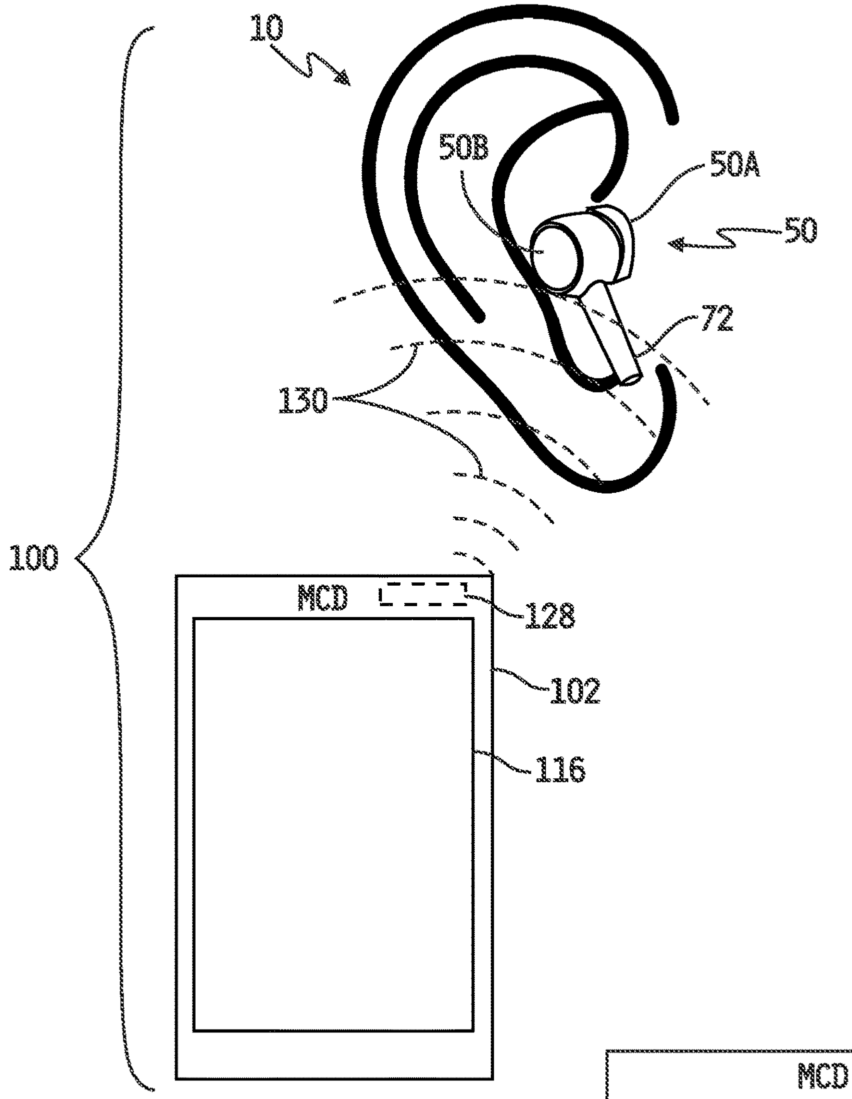
FIG. 5 is a simplified diagram of an embodiment of a photobiomodulation system showing another example of an external auditory canal photobiomodulation device, similar to that illustrated in FIGS. 2A-2D, placed in transdermal contact with the external auditory meatus of a human ear and controlled wirelessly by a software application executed by a mobile communication device.

Referring to FIG. 5, an embodiment is shown of a wirelessly control photobiomodulation system 100 in which a mobile communication device (MCD) 102 with wireless communication capability is configured, i.e., programmed, to control operation of at least one photobiomodulation device 50. In the illustrated embodiment, the external auditory meatus insertion portion 50A of the device 50 illustrated in FIGS. 2A-3 is placed in transdermal contact with the external auditory meatus of a human ear 10 as described above, and the control portion 50B of the device 50 which carries the electrical circuit 80 faces outwardly away from the ear 10 as shown. The MCD 102 is operable to communicate wirelessly with the electrical circuit 80 carried by the device 50 as depicted graphically in FIG. 5 by the wireless communication arcs 130, and is therefore operable to wirelessly control operation of the device 50. In one embodiment, the MCD 102 may be a conventional mobile cell phone, e.g., a so-called smart phone, although in alternate embodiments the MCD 102 may be provided in the form of other conventional or application-specific wireless communication devices. Example of such devices include, but are not limited to, a conventional personal data assistant (PDA), a tablet computer, a key fob, a smart watch, e.g., a standalone device or communicatively coupled to a mobile cell phone, a conventional wireless remote control device, or the like. In the embodiment illustrated in FIG. 5, the device 50 illustratively differs from that illustrated in FIGS. 2A-3 in that the device 50 illustrated in FIG. 5 includes a conventional stem 72 extending generally downwardly from the control portion 50B. The stem 72 may, in some embodiments, be open-ended, and in other embodiments the free end of the stem 72 may be closed, e.g., capped. In some embodiments which include the stem 72, the antenna 98, shown in FIG. 4 as being mounted to the circuit board 82, may extend at least partially into the stem 72. Alternatively or additionally, the stem 72 may house one or more conventional electronic components, examples of which may include, but are not limited to, one or more microphones, one or more force sensors, one or more batteries and/or other sources of electrical power, or other electrical and/or electromechanical devices.

Figure 6:
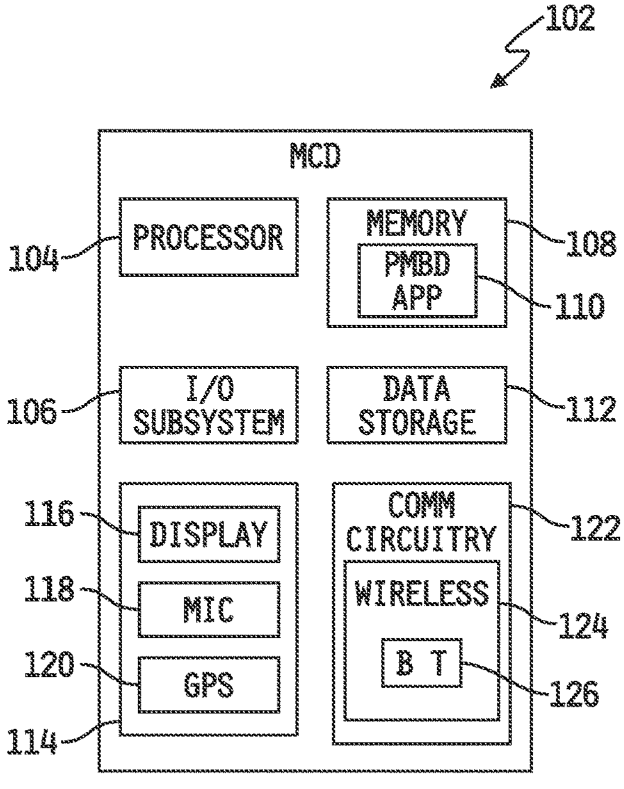
FIG. 6 is a simplified schematic block diagram of the mobile communication device of FIG. 5.

Referring now to FIG. 6, an embodiment of the MCD 102 is shown which illustratively includes a conventional processor 104 operatively coupled to an I/O subsystem 106 which is, in turn, coupled to a memory 108, a data storage 112, a number of peripheral devices 114 and communication circuitry 122. The memory 108 illustratively has stored therein a photobiomodulation device (PBMD) application 110 in the form of instructions executable by the processor 104 to control operation of the photobiomodulation device 50. The data storage 112 is illustratively implemented in the form of one or more conventional memory devices in which data relating to the user of the MCD 102 and/or data relating to operation of the device 50 is stored.

The peripheral devices 114 may include any conventional peripheral devices typically included on a mobile communication device 102 of the type just described. Examples include, but are not limited to, a conventional display screen 116, e.g., touch-controlled or otherwise, a conventional microphone 118 and a conventional GPS module (e.g., including a conventional GPS receiver and associated antenna). Those skilled in the art will recognize other conventional devices that may be included in the peripheral devices 114, and it will be understood that any such other conventional devices are intended to be included within the scope of this disclosure.

The communication circuitry 122 illustratively includes wireless communication circuitry 124, and the wireless communication circuitry 124 may illustratively include any number of wireless communication modules each configured to carry out wireless communications according to a particular communications protocol. Examples include, but are not limited to, Wi-Fi/internet communications, cellular communications, near-field communications, and the like. In the embodiment illustrated in FIG. 6, the wireless communication circuitry 124 alternatively or further includes a Bluetooth® module 126, e.g., in the form of a conventional Bluetooth® controller, that is electrically connected to a conventional Bluetooth® antenna 128 as illustrated by example in FIG. 5. As such, the MCD 102 is configured to conduct wireless communications with the photobiomodulation device 50 according to a conventional Bluetooth® communications protocol. In some embodiments, such wireless communications may be one-way; such that the MCD 102 may only wirelessly transmit information to the photobiomodulation device 50 and the photobiomodulation device 50 may only receive information wirelessly transmitted by the MCD 102, or vice versa, and in other embodiments such wireless communications may be two-way; such that the MCD 102 and the photobiomodulation device 50 may both wirelessly transmit information to, and receive information wirelessly transmitted by, the other.

In some embodiments in which the photobiomodulation device 50 includes wireless (or wired) communication capability as described above, the processor 104 of the MCD 102 is operable to control operation of the device 50 by executing the PBMD application 110 stored in the memory 108. In one embodiment, for example, at least one of the integrated circuits 92 mounted to the circuit board 82 of the device 50 is a conventional timer circuit coupled to the switch 90, and the PBMD application 110 illustratively includes instructions which, when executed by the processor 104, cause the processor 104 to control the wireless communication circuitry 126, 128 to wirelessly transmit one or more signals to the device 50 which carry(s) instructions to activate the timer circuit to cause the timer circuit to turn on and off the switch 90 at a predetermined pulse rate; e.g., 40 Hz. The Bluetooth® controller 96 on-board the device 50 is, in turn, operable to receive such instructions and to control the timer circuit to operate as just described. In other embodiments in which the pulse rate of the timer circuit is programmable, the PBMD application 110 illustratively includes instructions which, when executed by the processor 104, cause the processor 104 to control the wireless communication circuitry 126, 128 to wirelessly transmit one or more signals to the device 50 which carry(s) instructions to activate the timer circuit to cause the timer circuit to turn on and off the switch 90 at a selected pulse rate. In some embodiments, the duty cycle of the timer circuit may be static, e.g., 50%, and in other embodiments the duty cycle may be programmable and selectable as just described with respect to the pulse rate.

In other embodiments, at least one of the integrated circuits 92 mounted to the circuit board 82 of the device 50 may be a conventional processor coupled to, or including, a memory and to the switch 90, and such a memory may include instructions executable by the processor of the device 50 to cause the processor to control operation of the switch 90. In some such embodiments, the pulse rate and/or duty cycle of the irradiation sources 58A-58D may be static and in other embodiments may be selectable as described above.

In any case, the PBMD application 108 illustratively presents a user interface on the display screen 116 via which the user may selectively, i.e., via manual interaction with a touch-selectable interface displayed on the screen 16 and/or via manual selection of a button, switch or key of the MCD 102, control operation of the device 50 including use duration, e.g., 15-minute use intervals. In some embodiments, the PBMD application 108 may also provide for automatic capture of use data, e.g., calendar date, time of day, duration of use, location of use (e.g., via GPS data), etc., user entry of personal data, e.g., name, age, user activity level during use, user physiological and/or psychological state, e.g., hot, cold, calm, nervous, anxious, etc., and/or diagnostic data relating to operation of the device 50 (e.g., in embodiments in which the device 50 is configured to wirelessly transmit such data to the MCD 102).

Figure 7:
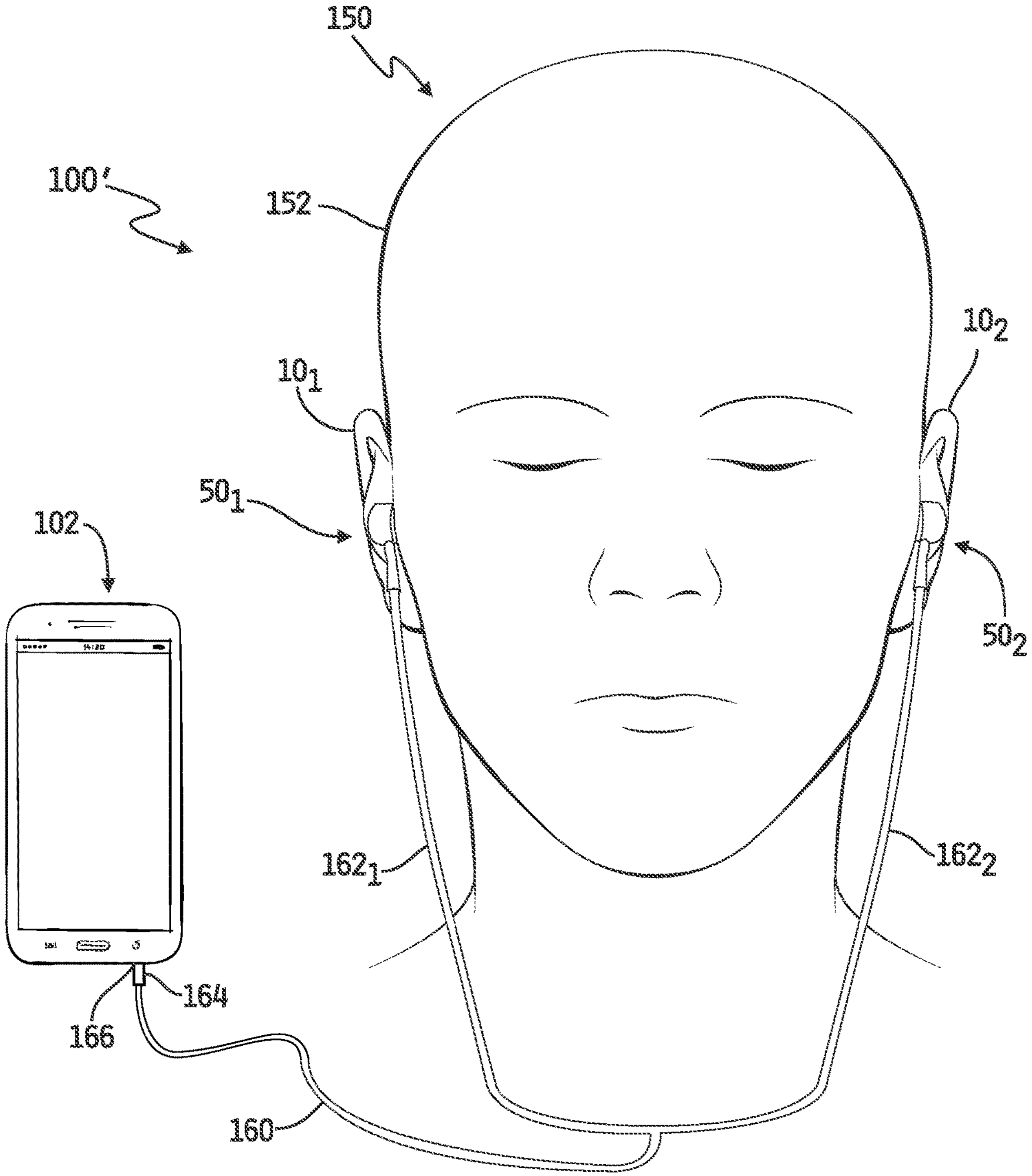
FIG. 7 is a simplified diagram another embodiment of a photobiomodulation system showing a pair of external auditory canal photobiomodulation devices, similar to that illustrated in FIGS. 2A-2D, each placed in transdermal contact with the external auditory meatus of a respective one of a pair of human ears and connected via a wired connection to a mobile communication device, wherein the photobiomodulation devices are controlled by a software application executed by the mobile communication device.

Referring now to FIG. 7, another embodiment is shown of a control photobiomodulation system 100' in which the mobile communication device (MCD) 102 is hard-wire connected, via a wiring harness 160, to two photobiomodulations devices $\mathbf{50}_1$, insertable into one ear $\mathbf{10}_1$, e.g., a right ear on a right side of a head 152 of a human, and $\mathbf{50}_2$, insertable into another ear $\mathbf{10}_2$, e.g., a left ear on a left side of the human head 152. In the illustrated embodiment, the photobiomodulation device $\mathbf{50}_1$ is operatively connected to one end of a wire assembly $\mathbf{162}_1$ of the wiring harness 160, the photobiomodulation device $\mathbf{50}_2$ is operatively connected to one end of another wire assembly $\mathbf{162}_2$ of the wiring harness 160, and the opposite ends of the wire assemblies $\mathbf{162}_1$ and $\mathbf{162}_2$ are merged together and operatively connected to a conventional electrical connector 164 configured to be received in mechanical and electrical engagement with a correspondingly configured port 166 defined on and in the MCD 102. In some embodiments, the MCD 102 is programmed, e.g., as described above, to control operation of the photobiomodulation devices $\mathbf{50}_1$, $\mathbf{50}_2$. In some alternate embodiments, either or both of the photobiomodulation devices $\mathbf{50}_1$, $\mathbf{50}_2$ (or any of the wireless photobiomodulation devices 50 described above) may include some or all of the circuitry required to operate them as described above. It will be understood that whereas two photobiomodulation devices $\mathbf{50}_1$, $\mathbf{50}_2$ are shown hard-wire connected to the MCD 102 in FIG. 7, alternate embodiments are contemplated in which the wiring harness 160 is configured to operatively couple more or fewer photobiomodulation devices to the MCD 102.

Use of the photobiomodulation device 50 illustrated in the attached figures and described herein may be used in either ear or in both ears 10 to provide therapeutic benefit to individuals suffering from any of a number of different physiological and/or psychological conditions. Examples of some such physiological and/or psychological conditions may include, but are not limited to, dementia, Alzheimer's disease, movement disorders generally (e.g., Parkinson's disease, as well as other movement disorders), peripheral inflammatory disorders, pulmonary edema, irritable bowel disorders, nausea, vomiting, respiratory disorders and related conditions, Tinnitus, Vertigo, migraine headaches, muscular tension-type headaches, temporomandibular joint dysfunction (TMJ) including, but not limited to, pain, inflammation, edema of the TMJ's and supporting structure(s), anxiety, depression, relaxation, bruxing, teeth clenching, restless leg syndrome, insomnia and/or as an adjunctive for sleep, acute pain conditions, and the like.

While this disclosure has been illustrated and described in detail in the foregoing drawings and description, the same is to be considered as illustrative and not restrictive in character, it being understood that only illustrative embodiments thereof have been shown and described and that all changes and modifications that come within the spirit of this disclosure are desired to be protected. For example, whereas the example photobiomodulation device 50 depicted in FIGS. 3 and 4 is illustrated as including an electrical circuit 80 mounted to a circuit board 82 and operatively coupled to irradiation sources 58A-58D, wherein the electrical circuit 80 includes circuit components for controlling operation of the irradiation sources 58A-58D, it will be understood that alternate embodiments are contemplated in which some or all of the electrical circuit 80 is omitted. In one non-limiting embodiment, for example, in which the photobiomodulation device 50 is configured to be hard-wire connected to a remote, mobile or stationary electronic control device, the electrical circuit 80 may be omitted in its entirety, and the mobile or stationary electronic control device may be electrically coupled directly to the irradiation sources 58A-58D via the hardwire connection such that the mobile or stationary device directly controls operation of the irradiation sources 58A-58D in the same manner as described hereinabove. Alternatively or additionally, the electrical circuit 80 in such embodiments may include one or more driver circuits electrically connected to the irradiation sources 58A-58D and electrically coupled directly to the mobile or stationary electronic control device via the hard-wire connection such that the mobile or stationary device controls operation of the irradiation sources 58A-58D via direct control of the one or more driver circuits. In either such example embodiment, the photobiomodulation device 50 may include one or more sources of electrical power, or may instead receive electrical power from the mobile or stationary device via the hard-wire connection.

What is claimed is:

1. A photobiomodulation device, comprising:

a housing having a first portion configured to be inserted into an external auditory meatus of a human ear and a second portion, at least one irradiation source coupled to the first portion of the housing such that at least a portion of a radiation emitting surface of the at least one irradiation source, upon insertion of the first portion of the housing into the external auditory meatus of the human ear, faces at least a portion of dermis of the external auditory meatus beneath which at least one of an arterial branch and a peripheral nerve branch of at least one cranial nerve is located, and an electrical circuit carried by the second portion of the housing and electrically connected to the at least one irradiation source, the electrical circuit including at least one circuit component for controlling the at least one irradiation source to irradiate the at least one of the arterial branch and the peripheral nerve branch of the at least one cranial nerve through the at least a portion of dermis of the external auditory meatus, wherein the at least the portion of the radiation emitting surface of the at least one irradiation source directs radiation radially outwardly from the first portion of the housing, wherein the at least one irradiation source includes light sources arrayed circumferentially on the first portion of the housing, thereby positioning each of the light sources opposite to, and facing, the at least one of the arterial branch and peripheral nerve branch of the at least one cranial nerve.

2. The photobiomodulation device of claim 1, wherein the first portion of the housing and the second portion of the housing are coupled together or are together of unitary construction, and wherein the first portion of the housing has a curved outer periphery.

3. The photobiomodulation device of claim 2, wherein the light sources include two or more light sources disposed radially about the curved outer periphery such that at least a portion of a radiation emitting surface of each of the two or more light sources faces a different portion of dermis of the external auditory meatus beneath which at least one peripheral nerve branch of a different respective cranial nerve is located.

4. The photobiomodulation device of claim 3, wherein the two or more light sources include four light sources disposed radially about the curved outer periphery of the first portion of the housing, each of the four light sources positioned approximately equidistant from one another about the curved outer periphery.

5. The photobiomodulation device of claim 1, wherein the at least one irradiation source is configured to produce radiation at a frequency in a range of visible red light or to produce radiation in a range of visible red light frequencies.

6. The photobiomodulation device of claim 1, wherein the at least one irradiation source comprises at least one light emitting diode (LED).

7. The photobiomodulation device of claim 1, further comprising a source of electrical power carried by the second portion of the housing.

8. The photobiomodulation device of claim 7, wherein the source of electrical power comprises at least one rechargeable or non-rechargeable battery.

9. The photobiomodulation device of claim 1, wherein the at least one circuit component includes at least one switch and a timer circuit operatively coupled to the at least one irradiation source, the timer circuit configured to control the at least one switch to cause the at least one irradiation source to pulse on and off.

10. The photobiomodulation device of claim 9, wherein the timer circuit is configured to control the at least one switch to cause the at least one irradiation source to pulse on and off at a predetermined or selectable pulse rate.

11. A photobiomodulation system, comprising:

the photobiomodulation device of claim 1, wherein the at least one circuit component includes wireless communication circuitry, and a mobile communication device including wireless communication circuitry configured to communicate wirelessly with the wireless communication circuitry of the photobiomodulation device, the mobile communication device further comprising a processor programmed to control operation of the at least one irradiation source of the photobiomodulation device by wirelessly communicating operating instructions to the wireless communication circuitry of the photobiomodulation device.

12. A photobiomodulation system, comprising:

the photobiomodulation device of claim 1, and a mobile communication device hard-wire connectable to the photobiomodulation device and including a processor programmed to control operation of the at least one irradiation source of the photobiomodulation device by communicating operating instructions to the at least one circuit component of the photobiomodulation device with the mobile communication device hard-wire connected to the photobiomodulation device.

13. A photobiomodulation apparatus, comprising:

a first photobiomodulation device having a first housing including a first portion configured to be inserted into an external auditory meatus of one ear of a human and a second portion, at least a first irradiation source coupled to the first housing such that at least a portion of a radiation emitting surface of the at least a first irradiation source, upon insertion of the first housing into the external auditory meatus of the one ear, faces at least a portion of dermis of the external auditory meatus of the one ear beneath which at least one of an arterial branch and a peripheral nerve branch of at least one cranial nerve is located, and a first electrical circuit carried by the first housing and configured to control the at least a first irradiation source to irradiate the at least one of the arterial branch and the peripheral nerve branch of the at least one cranial nerve through the at least a portion of dermis of the external auditory meatus of the one ear, wherein the at least the portion of the radiation emitting surface of the at least a first irradiation source directs radiation radially outwardly from the first housing, wherein the at least a first irradiation source includes light sources arrayed circumferentially on the first portion of the first housing, thereby positioning each of the light sources opposite to, and facing, the at least one of the arterial branch and peripheral nerve branch of the at least one cranial nerve.

14. The photobiomodulation apparatus of claim 13, wherein the first electrical circuit includes wireless communication circuitry, and wherein the apparatus further comprises a mobile communication device including wireless communication circuitry configured to communicate wirelessly with the wireless communication circuitry of the first photobiomodulation device, the mobile communication device further comprising a processor programmed to control operation of the at least a first irradiation source of the first photobiomodulation device by wirelessly communicating operating instructions to the wireless communication circuitry of the first photobiomodulation device.

15. The photobiomodulation apparatus of claim 14, further comprising a first source of electrical power carried by the first housing and operatively coupled to the at least a first irradiation source.

16. The photobiomodulation apparatus of claim 13, wherein the apparatus further comprises a mobile communication device hard-wire connectable to the first photobiomodulation device, the mobile communication device comprising a processor programmed to control operation of the at least a first irradiation source of the first photobiomodulation device by communicating operating instructions to the first electrical circuit with the mobile communication device hard-wire connected to the first photobiomodulation device.

17. The photobiomodulation apparatus of claim 16, further comprising a first source of electrical power carried by the first housing and operatively coupled to the at least a first irradiation source, or carried by the mobile communication device such that the mobile communication device supplies electrical power from the first source of electrical power to the first electrical circuit of the first photobiomodulation device with the mobile communication device hard-wire connected to the first photobiomodulation device.

18. The photobiomodulation apparatus of claim 13, further comprising:

a second photobiomodulation device having a second housing configured to be inserted into an external auditory meatus of the other ear of the human, at least a second irradiation source coupled to the second housing such that at least a portion of a radiation emitting surface of the at least a second irradiation source, upon insertion of the second housing into the external auditory meatus of the other ear, faces at least a portion of dermis of the external auditory meatus of the other ear beneath which at least one of an arterial branch and a peripheral nerve branch of at least one cranial nerve is located, and a second electrical circuit carried by the second housing and configured to control the at least a second radiation source to irradiate the at least one of the arterial branch and the peripheral nerve branch of the at least one cranial nerve through the at least a portion of dermis of the external auditory meatus of the other ear.

19. The photobiomodulation apparatus of claim 18, wherein the first electrical circuit includes first wireless communication circuitry and the second electrical circuit includes second wireless communication circuitry, and wherein the apparatus further comprises a mobile communication device including wireless communication circuitry configured to communicate wirelessly with the first wireless communication circuitry and the second wireless communication circuitry, and wherein the mobile communication device comprises a processor programmed to control operation of the at least a first irradiation source of the first photobiomodulation device and operation of the at least a second irradiation source of the second photobiomodulation device by wirelessly communicating operating instructions to the first wireless communication circuitry and to the second wireless communication circuitry.

20. The photobiomodulation apparatus of claim 18, wherein the apparatus further comprises a mobile communication device hard-wire connectable to the first and second photobiomodulation devices, the mobile communication device comprising a processor programmed to control operation of the at least a first irradiation source of the first photobiomodulation device and the at least a second irradiation source of the second photobiomodulation device by communicating operating instructions to the first and second electrical circuits with the mobile communication device hard-wire connected to the first and second photobiomodulation devices.

* * * * *